(12) United States Patent
Hyland et al.

(10) Patent No.: US 11,879,117 B2
(45) Date of Patent: Jan. 23, 2024

(54) GEL TRAY FOR BACTERIA TRANSFORMATION LAB

(71) Applicant: C.C. Imex, San Diego, CA (US)

(72) Inventors: Callen Elizabeth Hyland, La Jolla, CA (US); Christopher Karl Schroeder, San Diego, CA (US); Rita Mei Yi Wong, San Diego, CA (US); Richard Tat Lee Chan, La Jolla, CA (US)

(73) Assignee: C.C. Imex, San Diego, CA (US)

( * ) Notice: Subject to any disclaimer, the term of this patent is extended or adjusted under 35 U.S.C. 154(b) by 342 days.

(21) Appl. No.: 17/094,222

(22) Filed: Nov. 10, 2020

(65) Prior Publication Data

US 2022/0145225 A1    May 12, 2022

(51) Int. Cl.
  *C12M 1/12* (2006.01)
  *C12Q 1/18* (2006.01)
  *C12M 1/00* (2006.01)

(52) U.S. Cl.
  CPC ............ *C12M 23/04* (2013.01); *C12M 23/22* (2013.01); *C12Q 1/18* (2013.01)

(58) Field of Classification Search
  CPC ....... B01L 3/5085; C12M 25/06; C12M 23/04
  USPC ............................................ 435/305.2, 288.3
  See application file for complete search history.

(56) References Cited

U.S. PATENT DOCUMENTS

| | | | | |
|---|---|---|---|---|
| 4,054,490 A | * | 10/1977 | Vesterberg | C12M 23/34 435/304.2 |
| 4,204,045 A | * | 5/1980 | Kjellander | C12M 41/36 220/555 |
| 4,271,270 A | | 6/1981 | Lukacsek | |
| 6,180,065 B1 | * | 1/2001 | Homola | B01L 3/5085 422/547 |
| 6,432,663 B1 | * | 8/2002 | Seip | C12M 23/34 435/283.1 |
| 2003/0157706 A1 | * | 8/2003 | Hamilton | C12N 1/18 435/325 |
| 2014/0196550 A1 | * | 7/2014 | Chernomorsky | C12M 23/12 73/864.91 |

FOREIGN PATENT DOCUMENTS

| | | | |
|---|---|---|---|
| CN | 106591127 | * | 4/2017 |
| CN | 106591127 A | | 4/2017 |

(Continued)

OTHER PUBLICATIONS

Heathrow Scientific. "Dual Solution Reservoir" Published from Internet Archive Wayback Machine : Jun. 11, 2016. Accessed : Feb. 25, 2023. https://web.archive.org/web/20160611063405/https://www.heathrowscientific.com/dual-solution-reservoir-i-hea20821a (Year: 2016).*

(Continued)

*Primary Examiner* — Michael L Hobbs
*Assistant Examiner* — Nathan G Esperon
(74) *Attorney, Agent, or Firm* — John L. Rogitz

(57) ABSTRACT

A gel tray for a bacteria transformation lab exercise has a transparent plastic body with four parallel gel channels and four filling ports, one for each channel into which unmodified bacteria and heat-shocked bacteria can be injected by students along with appropriate reaction constituents to demonstrate transformation of the bacteria under visualization.

7 Claims, 5 Drawing Sheets

(56) References Cited

FOREIGN PATENT DOCUMENTS

| EP | 0402888 A1 | 12/1990 | | |
|----|----|----|----|----|
| WO | WO-9747388 A1 | * | 12/1997 | ............ B01L 3/5085 |

OTHER PUBLICATIONS

Stoebel. "The Cost of Expression of *Escherichia coli* lac Operon Proteins Is in the Process, Not in the Products". 2008. The Genetics Society of America. DOI: 10.1534/genetics. 107.085399 (Year: 2008).*

Johnsen. "Engineering Increased Stability in the Antimicrobial Peptide Pediocin PA-1" Applied and Environmental Microbiology, Nov. 2000, p. 4798-4802 vol. 66, No. 11 (Year: 2000).*

* cited by examiner

GEL TRAY FOR BACTERIA TRANSFORMATION LAB

FIELD

This application relates to gel trays for bacterial growth, including genetic transformation labs.

BACKGROUND

The present assignee's U.S. Pat. No. 9,835,587, incorporated herein by reference, discloses a commercially successful electrophoresis running tank assembly for use in the classroom to aid students in learning modern DNA assay techniques.

SUMMARY OF THE INVENTION

Present principles are directed to a plastic tray with plural channels to hold bacterial growth medium for the purpose of viewing bacterial growth or behavior. Current methods of growing bacteria are generally intended for professional laboratory personnel. The protocol and process are time consuming, cumbersome, and unreliable for high school education. Students need a system that allows them to reliably get the intended results while performing steps that mirror everyday biotech research and development.

One application is observing the results of bacterial transformation, the introduction of new behavior in bacteria through the introduction of foreign DNA. This behavior can include antibiotic resistance, fluorescence, or production of a desired protein. Introduction of antibiotic resistance into a previously antibiotic sensitive bacteria strain via DNA is a seminal discovery that forms an important foundation of biotechnology. The importance of bacterial transformation in the field of biotechnology makes it a key concept to be taught in high schools and colleges. Control of gene expression is also an important concept in biotechnology.

Accordingly, a gel tray includes a transparent body and plural (e.g., four) gel channels formed in the body parallel to each other. Plural filling ports, each having a fill end for receiving samples and a channel end communicating with an end of a respective one of the gel channels, define respective axes from the respective fill end to the respective channel end.

In some examples an oblique angle is established between the axis of at least one of the filling ports and a longitudinal axis of its respective gel channel.

In example implementations the fill ends are elevated above the channel ends on the body.

If desired, at least one constituent can be in the gel channels to deter the growth of microbes during storage. For example, an antibiotic such as ampicillin can be added to the gel. An additional constituent may induce the expression of exogenous genes, for example monosaccharide Isopropyl beta-d-1-thiogalactopyranoside (IPTG).

Respective gels may be disposed in the gel channels.

In example embodiments unmodified bacteria host cells can be added in a first one of the gel channels. Unmodified bacteria host cells and an antibiotic such as ampicillin can be added in a second one of the gel channels, and genetically modified (such as by heat-shocking or with a gene gun) bacteria host cells and a plasmid can be added in a third one of the gel channels. Genetically modified bacteria host cells, antibiotic, and a chemical to induce expression of an exogeneous constituent, e.g. IPTG, can be added in a fourth gel channel.

In another aspect, a method includes adding unmodified bacteria host cells to a first receptacle of a gel tray and adding unmodified bacteria plus an antibiotic, such as ampicillin, to a second receptacle of the gel tray. The method also includes adding genetically modified bacteria and antibiotic to a third receptacle in the gel tray and adding the genetically modified bacteria along with antibiotic and a chemical to induce exogenous expression to a fourth receptacle in the gel tray. The gel tray is illuminated to permit visualization of fluorescence therein.

In another aspect, a gel tray, e.g., for a bacteria transformation observation includes a transparent plastic body with plural (e.g., from two to ten and in specific examples four) parallel gel channels into which unmodified bacteria and genetically modified bacteria can be added along with appropriate reaction constituents to demonstrate transformation of the bacteria under visualization.

In another aspect, a gel tray includes a transparent plastic body with plural gel channels into which unmodified host bacteria and genetically modified bacteria along with appropriate reaction constituents are added. To demonstrate transformation, reaction constituents, e.g. a monosaccharide, induce fluorescence under visualization with light that excites fluorescent molecules expressed by the genetically modified bacteria. In one example, a gel tray with plural channels is placed on an apparatus that illuminates the gel tray with light of a specific wavelength or range of wavelengths (e.g. 475 nm) that excites a fluorophore expressed by genetically modified bacteria. Light used in illumination may be blocked by a colored filter. In another example, a gel tray with plural channels is placed on an apparatus that illuminates one of the channels with a specific wavelength of light while simultaneously illuminating one or more of the additional channels with a different specific wavelength of light to visualize excitation of two or more different fluorophores simultaneously with the apparatus providing barriers between the channels to block light in one channel from illuminate an adjacent channel.

The details of the present application, both as to its structure and operation, can best be understood in reference to the accompanying drawings, in which like reference numerals refer to like parts, and in which:

DETAILED DESCRIPTION

Figure 1:
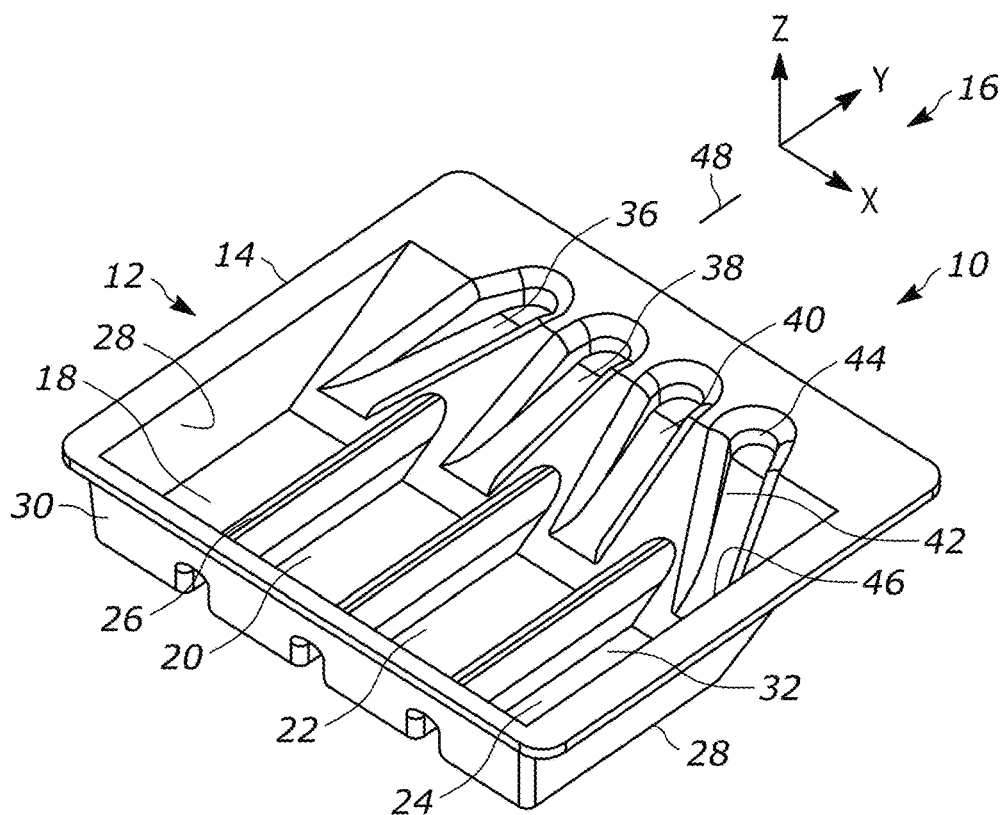
FIG. 1 is an isometric view of the gel tray when empty from a top perspective.
Figure 2:
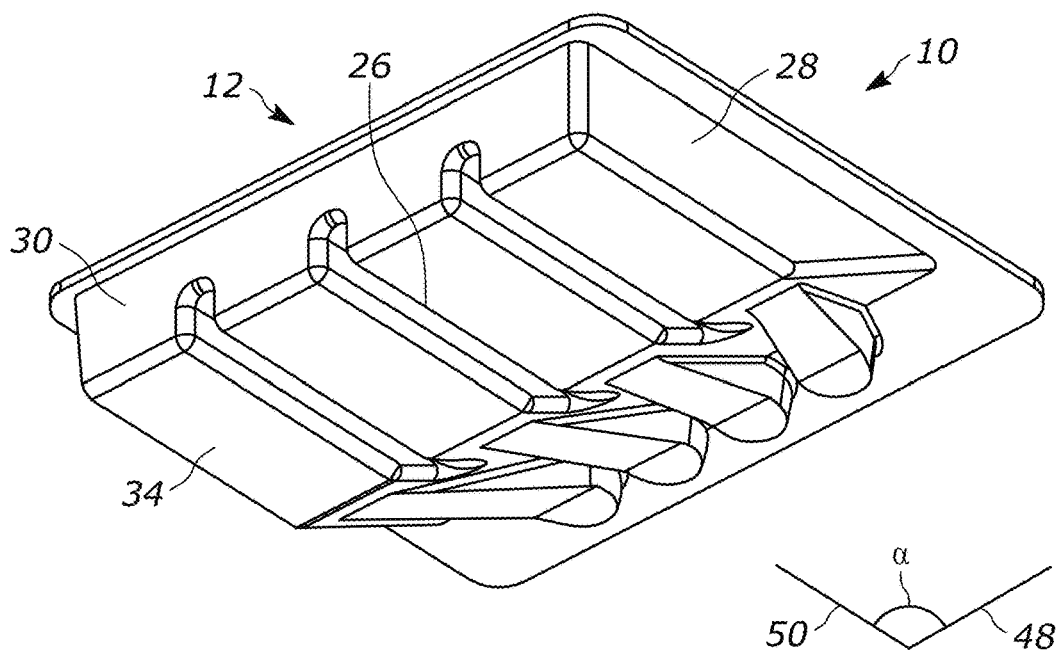
FIG. 2 is an isometric view of the gel tray when empty from a bottom perspective.

Referring initially to FIGS. 1 and 2, an assembly is shown, generally designated 10, which can be used for observing bacterial growth, is particularly, although not exclusively suited for academic use by students. The assembly 10 includes a transparent plastic body 12 with a generally parallelepiped-shaped periphery 14 in an x-y (horizontal) plane indicated by the axes 16 that is established when the body 12 is oriented as operationally intended on a viewing assembly as discussed further below. The body 12 may be a unitary piece of plastic formed by, e.g., injection molding.

In the example shown, first through fourth gel channels 18, 20, 22, 24 are formed in the body 12 parallel to each other, although in other embodiments a fewer or greater number of gel channels may be used, e.g., any integer number of gel channels from two on up. The gel channels are separated from each other by raised elongated ribs 26 that are parallel to the gel channels and that are elongated in the same dimension as the gel channels are elongated. The outer gel channels 18, 24 are thus bounded by respective vertical sidewalls 28 of the body 12 and on their sides opposite the sidewalls 28 by a respective rib 26, while the inner gel channels 20, 22 are bounded on both sides by ribs 26. The gel channels extend in length from a common end wall 30 to respective channel ends 32, and the bottom walls 34 of the gel channels 18-24 lie in the horizontal plane.

Extending upwardly (in the z-dimension) from the horizontal gel channels at oblique angles to the horizontal plane if desired, are first through fourth filling ports 36, 38, 40, 42, each having a respective fill end 44 that may have a semi-circular circumference if desired as shown. More generally, a filling port may be provided for each gel channel. The fill ends are configured for receiving constituent samples from a dispenser such as a micropipette or multichannel pipette. Each filling port 36-42 extends from its fill end 44 to a respective channel end 46 that communicates with a respective channel end 32 of a respective one of the gel channels. The fill ends 44 thus may be elevated above the channel ends 46 of the fill ports on the body.

The respective channel ends 32, 46 of a respective gel channel/filling port pair are closely juxtaposed as shown such that constituent deposited in the fill end 44 of a filling port flows down the filling port under gravity through the channel ends 32, 46 and into the respective gel channel. In the example shown, each filling port is elongated from end 44 to end 46 and defines an axis there between with a component 48 in the horizontal plane. As best shown in FIG. 2, an oblique angle $\alpha$ can be established between the axis component 48 of at least one of the filling ports and a longitudinal axis 50 of its respective gel channel.

Figure 3:
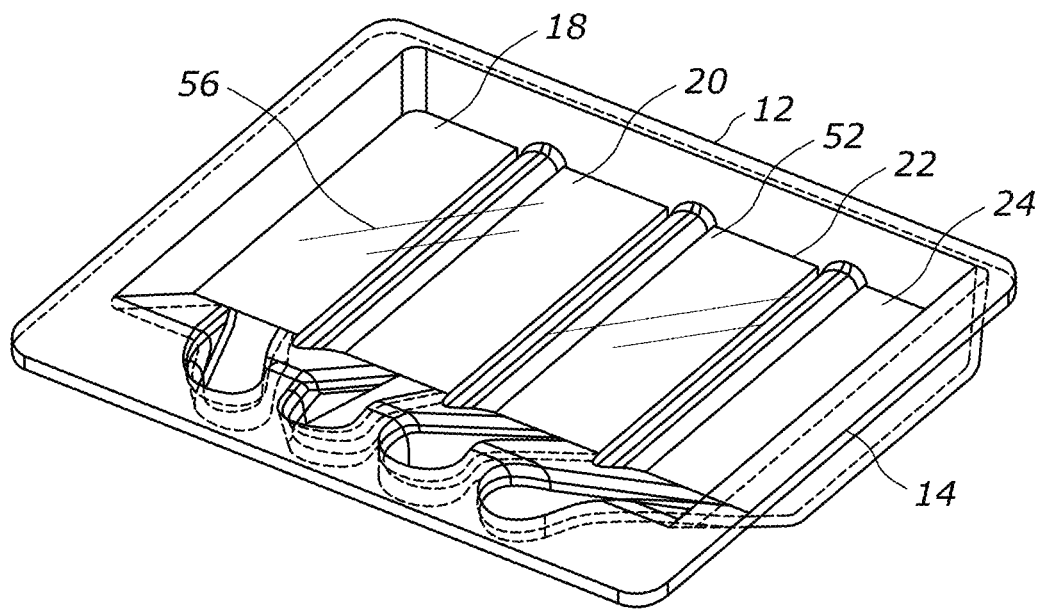
FIG. 3 is an isometric view of the gel tray when filled with gel and covered with film.

FIG. 3 illustrates that respective gels 52 may be disposed in the first through fourth gel channels 18-24 on the bottoms thereof. The gels 52 may contain a constituent to deter the growth of microbes during storage. In one example, the gels 52 are essentially growth media and may be composed of, e.g., lysogeny broth agar that contains chloramphenicol to deter the growth of wild bacteria, yeast, or other microbes during storage.

A transparent protective plastic sheet 56 may cover the interior of the body 12 as shown and may extend across the periphery 14 from all four sides (FIG. 3 illustrates the transparent sheet 56 by means of shading lines.) The assembly shown in FIG. 3 may be vended to end users who can then add constituents to one or more of the gels 52 as discussed further below. Or the body 12 alone may be vended to end users who can fill the gel channels 18-24 with the gels 52.

It may now be appreciated that the gel tray assembly 10 may include four separate pools of growth media (gels), for example, one for a control and three for variations. The body 12 of the tray is transparent (which include translucent) to allow light to pass through the bottom 34 and into the contents of the gel channels 18-24 tray.

Figure 4:
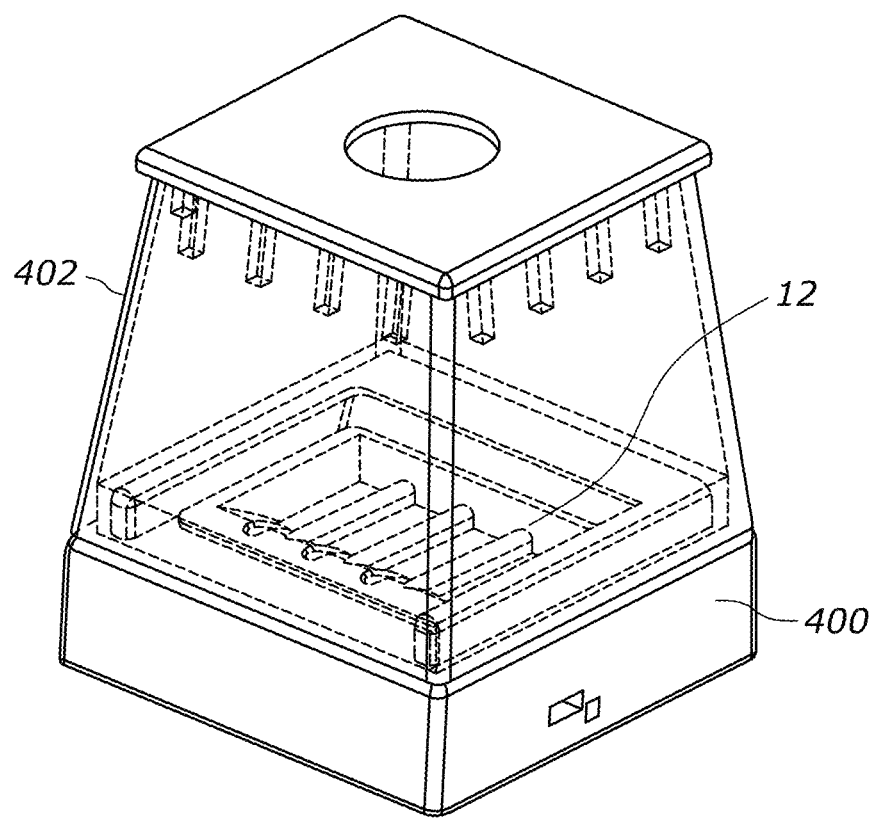
FIG. 4 is an isometric view of the gel tray in a viewer.
Figure 5:
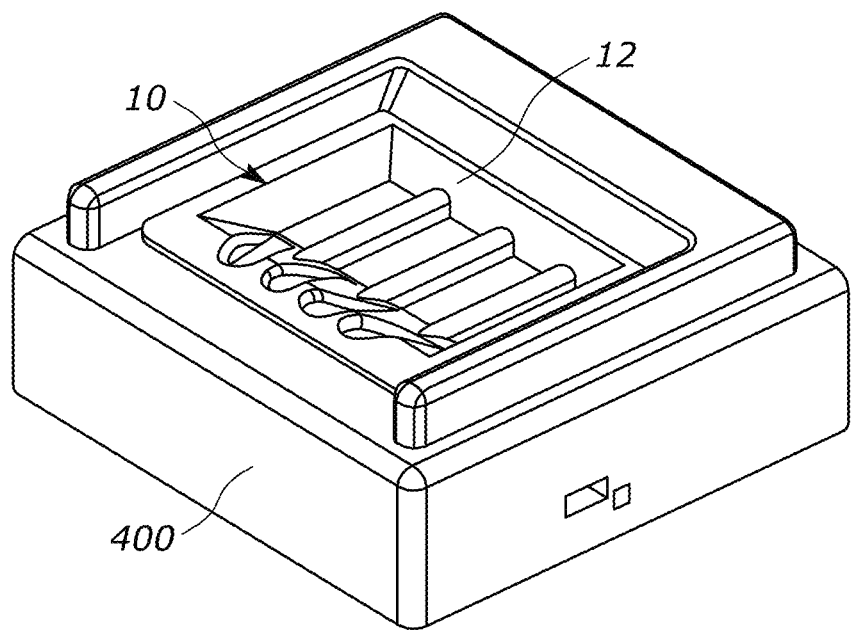
FIG. 5 is an isometric view of the gel tray on a viewer base.

FIGS. 4 and 5 illustrate that the body 12 of the gel tray is designed to fit onto a base 400 of a viewing assembly such as but not limited to that described in the referenced U.S. patent, to be covered by a hood 402 such as the hood described in the referenced U.S. patent, with the base 400 including lamps to illuminate the tray assembly 10 from below and photograph the tray assembly from above through an optical filter to detect and record presence of bacteria colonies and whether or not they exhibit fluorescence. The base 400 and hood 402 alternatively may be implemented by a simpler design apart from that referenced in the U.S. patent, marketed by the instant assignee under the trade name "The Winston™". The body 12 of the tray assembly 10 is designed to be easily filled, sterilized, and sealed to meet storage and shipping requirement, and to be easily unsealed by removing the sheet 56 to allow a student to introduce bacterial samples and subsequently resealed to allow for effective incubation of the experiment. The base 400 or other component may include heaters and/or coolers such as thermoelectric coolers to maintain temperature of constituents in the gel tray. Also, illumination may be from the sides or even top of the gel tray in addition to or in lieu of bottom illumination.

Unmodified bacteria host cells may be disposed in the first gel channel 18 by an end user. Such cells may be, in one example, a strain (BL21) of *E. coli* bacteria that already has resistance to chloramphenicol.

In one example implementation, unmodified bacteria and an antibiotic may be added to the second gel channel 20 by an end user. For example, ampicillin may be used to demonstrate that this antibiotic will kill bacteria that have not been transformed with an ampicillin resistance gene. Antibiotics other than ampicillin may be used.

Added to the third gel channel 22 may be genetically modified bacteria such as bacteria transformed with a plasmid (vector) through heat-shocking or another method. Prior to heatshocking, bacteria may be made competent by the addition of a chemical, for example, calcium chloride. The plasmid (vector) may include genes for making fluorescent protein molecules like eGFP (enhanced Green Florescent Protein), which glows green under blue light when the bacteria makes it. The plasmid may also include an ampicillin resistance gene. That way ampicillin can be used to kill all of the bacteria that do not take up the plasmid.

Into the fourth gel channel 24 may be added by an end user genetically modified bacteria along with an antibiotic and a chemical, e.g. IPTG, to induce expression of an exogenous constituent, as described above. A plasmid vector may be incorporated which can be a plasmid developed specifically for the purpose of lab activity that gives the bacteria resistance to ampicillin and, when activated by IPTG, induces the bacterial to produce a protein that is fluorescent (eGFP).

Preferably, the samples added to all gel channels are spread evenly over the surface of the agar to maximize growth. The tray is sealed again with the sheet 56 and incubated.

Figure 6:
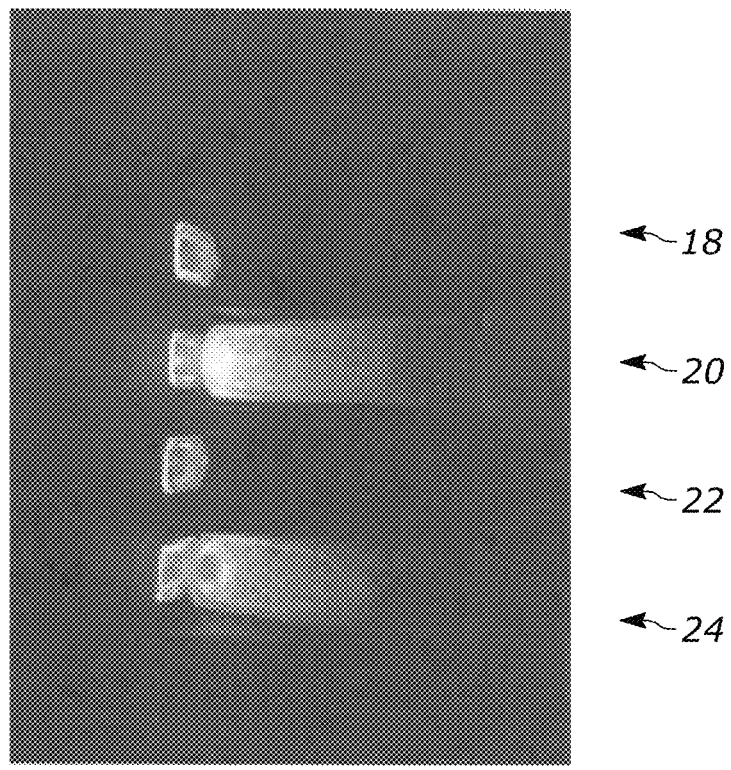
FIG. 6 shows colonies of genetically modified bacteria, transformed with a plasmid containing the gene for eGFP, growing on a petri dish containing LB medium agar with chloramphenicol, ampicillin, and IPTG.
Figure 7:
FIG. 7 shows colonies of genetically modified bacteria, transformed with a plasmid containing the gene for eGFP, growing in plastic tubes containing LB medium agar with chloramphenicol, ampicillin, and IPTG.

FIGS. 6 and 7 illustrate expected results.

Figure 8:
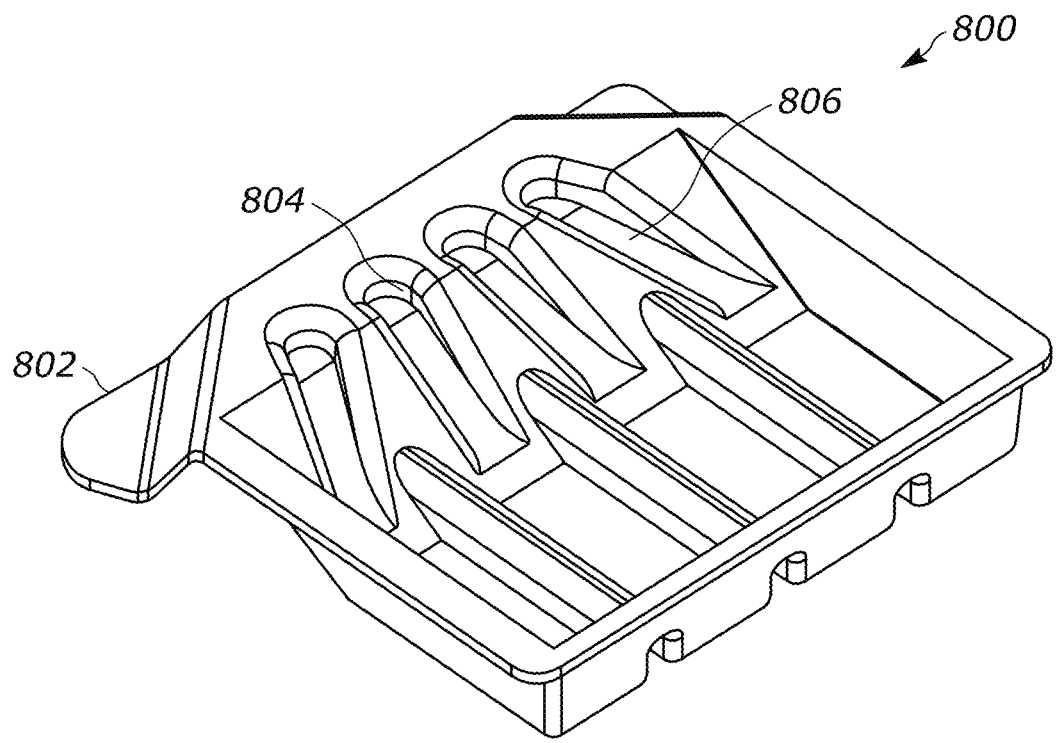
FIG. 8 is an isometric view of an alternate embodiment.

FIG. 8 illustrates a gel tray 800 that in all essential respects is identical in configuration and operation to the gel tray(s) shown previously with the following exception. The gel tray 800 in FIG. 8 includes tabbed corners 802 extending down and away from fill ends 804 of fill ports 806 to aid in removing the protective sheet discussed previously.

Figure 9:
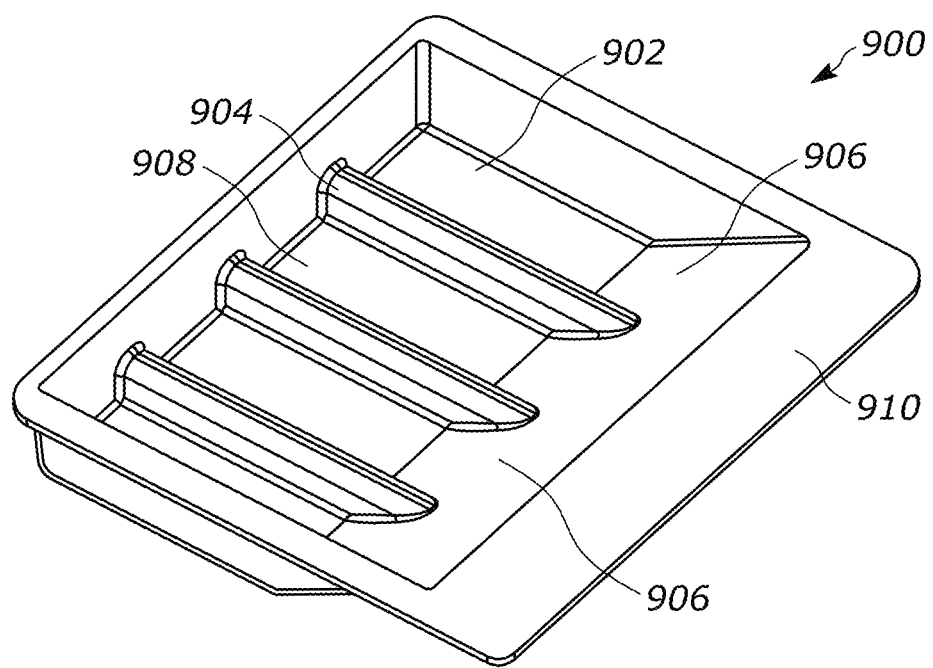
FIGS. 9 and 10 illustrate an alternate embodiment.
Figure 10:
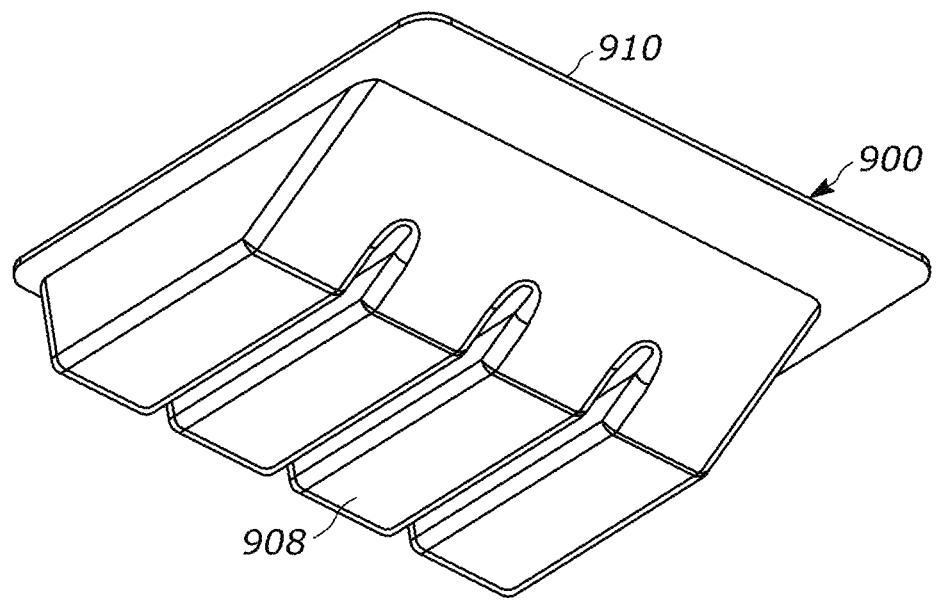

FIGS. 9 and 10 illustrate a gel tray 900 in all essential respects is identical in configuration and operation to the gel tray(s) shown previously with the following exception. The gel tray 900 in FIGS. 9 and 10 includes no separate fill ports, and includes plural (e.g., four) gel channels 902 separated by ribs 904 and terminating in a slanted wall 906 that extends upwardly and outwardly from the ends of bottoms 908 of the gel channels 902 at an oblique angle to the bottoms 908 to terminate in a flat edge flange 910 that is generally parallel to the bottoms 908 of the channels 902.

While particular structures and techniques are herein shown and described in detail, it is to be understood that the subject matter which is encompassed by the present invention is limited only by the claims.

What is claimed is:

1. A gel tray comprising:
   a body;
   plural gel channels formed in the body parallel to each other; and
   plural filling ports each having a fill end for receiving samples and a channel end communicating with an end of a respective one of the gel channels, each filling port defining an axis from the respective fill end to the respective channel end, the gel channels formed in the body, the gel channels being separated from each other by raised elongated ribs that are parallel to the gel channels and that are elongated in a same dimension as the gel channels are elongated such that outer gel channels are bounded by respective vertical sidewalls of the body and on their sides opposite the sidewalls by a respective rib, while inner gel channels are bounded on both sides by ribs, the gel channels extending in length from a common end wall of the body to respective channel ends, bottom walls of the gel channels lying in a common plane, the filling ports extending upwardly from the gel channels at oblique angles to the common plane, each fill end having a curvilinear circumference, the fill ends being elevated above the channel ends, each filling port being elongated from end to end, an oblique angle being established between the axis of at least one of the filling ports and a longitudinal axis of its respective gel channel.

2. The gel tray of claim 1, comprising at least one constituent in the gel channels to deter the growth of microbes during storage.

3. The gel tray of claim 1, comprising respective gels in the gel channels.

4. The gel tray of claim 3, comprising unmodified bacteria host cells in a first one of the gel channels.

5. The gel tray of claim 3, comprising unmodified bacteria host cells and an antibiotic in a second one of the gel channels.

6. The gel tray of claim 3, comprising genetically modified bacteria host cells and a plasmid in a third one of the gel channels.

7. The gel tray of claim 3, comprising genetically modified bacteria host cells, an antibiotic, and a chemical to induce exogenous expression in a fourth one of the gel channels.

* * * * *